United States Patent [19]

Robles et al.

[11] Patent Number: 5,377,234
[45] Date of Patent: Dec. 27, 1994

[54] COLLOIDAL RESIN SLURRY RECYCLE CONCENTRATING SYSTEM OF NUCLEAR REACTOR COOLANT WATER

[75] Inventors: Michel N. Robles, Livermore; Dane T. Snyder, Byron, both of Calif.

[73] Assignee: General Electric Company, San Jose, Calif.

[21] Appl. No.: 965,323

[22] Filed: Oct. 23, 1992

[51] Int. Cl.⁵ .................................. G21C 17/00
[52] U.S. Cl. .................... 376/245; 376/313; 376/305
[58] Field of Search ............. 376/310, 305, 245, 253, 376/313, 685; 210/660

[56] References Cited

U.S. PATENT DOCUMENTS

| | | | |
|---|---|---|---|
| 3,962,078 | 6/1976 | Hirs | 210/27 |
| 3,971,842 | 7/1976 | Ewbank | 423/7 |
| 4,120,786 | 10/1978 | Petersen et al. | 209/454 |
| 4,200,612 | 4/1980 | Lamaze | 423/70 |
| 4,252,644 | 2/1981 | Small et al. | 210/656 |
| 4,699,718 | 10/1987 | Jones et al. | 210/659 |
| 4,880,595 | 11/1989 | Matsuda et al. | 376/313 |
| 5,192,446 | 3/1993 | Salem et al. | 210/685 |
| 5,208,165 | 5/1993 | Law et al. | 436/176 |

Primary Examiner—Donald P. Walsh
Assistant Examiner—Meena Chelliah
Attorney, Agent, or Firm—J. S. Beulick

[57] ABSTRACT

An analytical testing means for determining the ion contents of nuclear reactor coolant water comprising ion chromatograph means and a conductivity detector. Reagent containing ion exchange resin is recycled, concentrated and the ion exchange resin regenerated to provide a more economic procedure.

4 Claims, 3 Drawing Sheets

COLLOIDAL RESIN SLURRY RECYCLE CONCENTRATING SYSTEM OF NUCLEAR REACTOR COOLANT WATER

FIELD OF THE INVENTION

This invention relates to the analytical testing of the coolant water circulating throughout a water cooled and moderated nuclear fission reactor plant. The invention comprises an improvement in such analytical testing apparatus comprising means for recovering, concentrating and reconstituting a reagent containing ion exchange resin in slurry form.

BACKGROUND OF THE INVENTION

Typical boiling water and pressurized water nuclear fission reactor plants comprise a nuclear fission reactor having an enclosed body of heat producing fissionable fuel which is associated with steam driven turbines for propelling electrical generators. Reactor coolant water is continuously circulated through the system during normal operation to carry the produced heat energy away from the fuel core for the formation of steam to be expended in work driving a turbine. Thus utilized coolant water and/or steam condensate is in turn cycled back into the nuclear reactor to repeat its heat energy transferring circuit substantially endlessly. This repeated circulation of coolant water throughout a vast network of vessels and conduits composed of different materials, chemical and physical conditions including temperatures, pressures and radiation, and products of radiation commonly containing corrosive agents, requires constant monitoring of the chemistry of the circulating coolant water from different locations throughout the system.

Common analytical testing procedures for nuclear fission reactor coolant water comprise sequentially sampling individual water specimens from many diverse locations throughout the nuclear reactor coolant water circulating system. The sampled coolant water specimens are each transferred through a network of coolant water sample conveying conduits or tubes to a central or consolidated water analyzing instrument. The water testing instrument analyzes each specimen in sequence for determining the presence of designated constituents such as chloride, sodium, potassium, sulfate, etc. and their concentrations dissolved within the coolant water samples. This soluble constituent data derived from various coolant water samples provides a basis for modifying the water chemistry as a means of controlling the content of components causing corrosion or radiation and the like potentially deleterious conditions within the coolant water circulating system.

Typical of nuclear reactor coolant water testing or monitoring apparatus comprising ion chromatographic means and water analysis procedures is the disclosure of U.S. Pat. No. 4,472,354, issued Sep. 18, 1984. The disclosure and contents of the aforesaid U.S. Pat. No. 4,472,354 is incorporated herein by reference.

SUMMARY OF THE INVENTION

This invention constitutes an improvement in an analytical testing apparatus wherein a reagent used in the measurement process is recycled by recovering and concentrating the ion exchange resin content of the analytical waste for reuse.

OBJECTS OF THE INVENTION

It is a primary object of this invention to provide an improved analytical testing apparatus for determining the soluble contents of nuclear reactor coolant water.

It is an additional object of this invention to provide an analytical testing apparatus which accurately evaluates soluble ions within the coolant water of a nuclear fission reactor cooling system.

It is another object of this invention to provide an ion chromatographic system for determining the soluble contents of coolant water throughout the coolant circuit of a nuclear reactor and recycling the ion exchange resin-containing effluent.

It is still another object of this invention to provide an ion chromatographic apparatus for analyzing nuclear reactor coolant water for its soluble contents which concentrates the ion exchange resin-containing effluent for reuse, thereby providing a substantial cost savings.

It is also an object of this invention to provide an economical and effective means of testing for the soluble ion contents of nuclear reactor coolant water comprising recycling and concentrating ion exchange resin contents of an effluent consisting of sampled specimens of nuclear reactor coolant water.

DETAILED DESCRIPTION OF THE INVENTION

Figure 1:
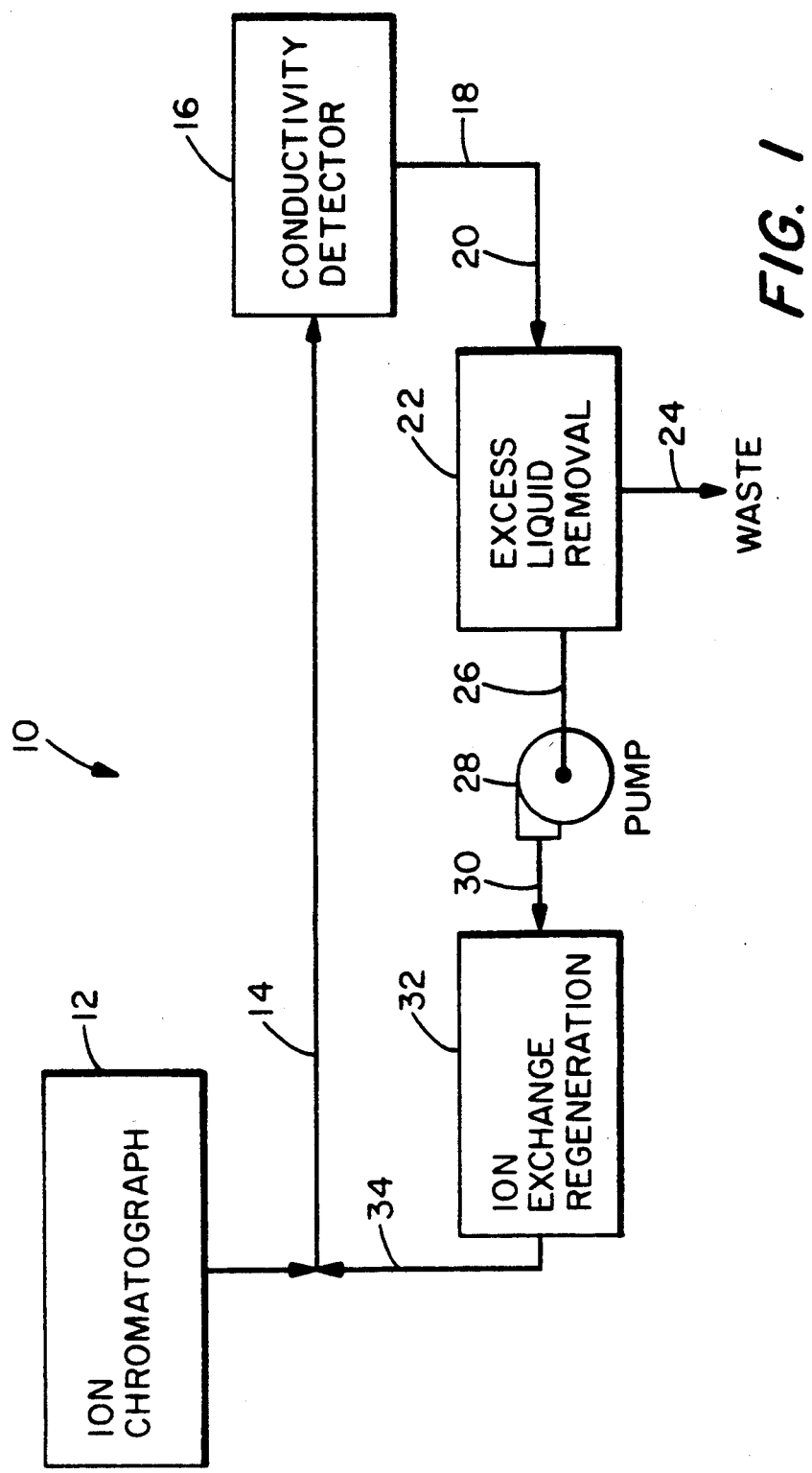
FIG. 1 is a block diagram illustrating the combined assembly of components of the subject invention.

Ion chromatography techniques of the prior art use an ion exchange column and an ionic mobile phase, termed eluent, to separate ionic analytes for measurement by a conductivity detector. Various means have been proposed to improve the sensitivity and signal-to-noise ratio of an ion chromatograph operation or system. One means consists of ion exchange columns or membranes that chemically neutralize (reduce) the conductivity of the eluent while enhancing (increasing) the conductivity of the analyte ions, thereby providing extremely sensitive conductimetric detection. Another means for achieving such chemical reduction of eluent conductivity and enhancement of analyte conductivity comprises injecting a slurry of very fine ion exchange particles, sometimes referred to as a solid phase reagent, into the eluent stream as it egresses from the ion exchange column. This produces chemical changes in the eluent that provide for very sensitive conductimetric detection.

A significant disadvantage of the latter ion exchange additive means is the high costs of such ion exchange materials.

In accordance with this invention, means are provided for a recycling operation incorporating an ion exchange process with ultrafiltration whereby an element of a sampled water specimen comprising a colloidal resin slurry is passed through a filter to concentrate its ion exchange resin contents by removing excess liquid phase as filtrate, then regenerating the concentrated ion exchange materials to form a concentrated resin slurry or so-called solid phase reagent. Thus rejuvenated, the concentrated reagent with regenerated exchange material is combined with the effluent from the ion chromatograph column and returned to the conductivity detector. A pump is employed to impel the reagent containing the colloidal resin slurry through the recycling circuit from the conductivity detector and back.

Referring to the drawings, the ion chromatograph apparatus 10 for testing of ion contents of nuclear reactor coolant water, comprises at least one ion chromatography device 12 for monitoring any ion contents of sampled water specimens. The ion chromatograph 12 monitors inorganic anions, monovalent cations, divalent cations or anions of organic acids. In accordance with this invention, ion exchange material is added to the effluent from the ion chromatograph 12 by any suitable means. A conduit 14 provides fluid communication for eluent from the discharge outlet of the ion chromatograph 12 to the downstream inlet of a conductivity detector 16 which ascertains the ion contents of the eluent.

Pursuant to one embodiment of this invention, the ion chromatograph 12 and conductivity detector 16 are combined in an assembly with a recycling circuit 18 including a given sequence of stations or units and functions for receiving the eluent effluent from the conductivity detector 16. Namely, conduit 20 provides fluid communication from the conductivity detector outlet to a filter unit 22 having a filtrate discharge 24, conduit 26 provides fluid communication from the filter unit 22 outlet into a pump 28 for impelling the concentrated reagent through the recycling circuit 18 including the units therein and back to the conductivity detector 16, conduit 30 provides fluid communication from the pump unit 28 into an ion exchange regeneration unit 32, and conduit 34 provides fluid communication from the ion exchange regeneration unit 32 into conduit 14 for injecting recycled reagent back into the conductivity detector 16 along with any newly introduced eluent from the ion chromatograph 12.

Filter unit 22 concentrates the ion exchange resin content of the effluent from the conductivity detector 16 by removing excess liquid phase therefrom as filtrate which is dispensed as waste through discharge duct 24. Backpressure within the recycling circuit 18 forces excess liquid out through the filter medium, thereby reducing the liquid phase of the resin slurry. The pore size of the filter medium employed is smaller than the particle size of the slurried ion exchange resin to preclude its loss with the filtrate. As noted, pump 28 propels the reagent comprising the colloidal resin slurry through the recycling circuit 18 from the conductivity detector 16 and back again. The ion exchange regeneration unit 32 regenerates the ion exchange material introduced into the eluent dispensed from the ion chromatograph 12 and carried therein as a colloidal resin slurry. Regeneration rejuvenates the action of the ion exchange material to chemically neutralize eluent conductivity and enhance analyte conductivity.

Figure 2:
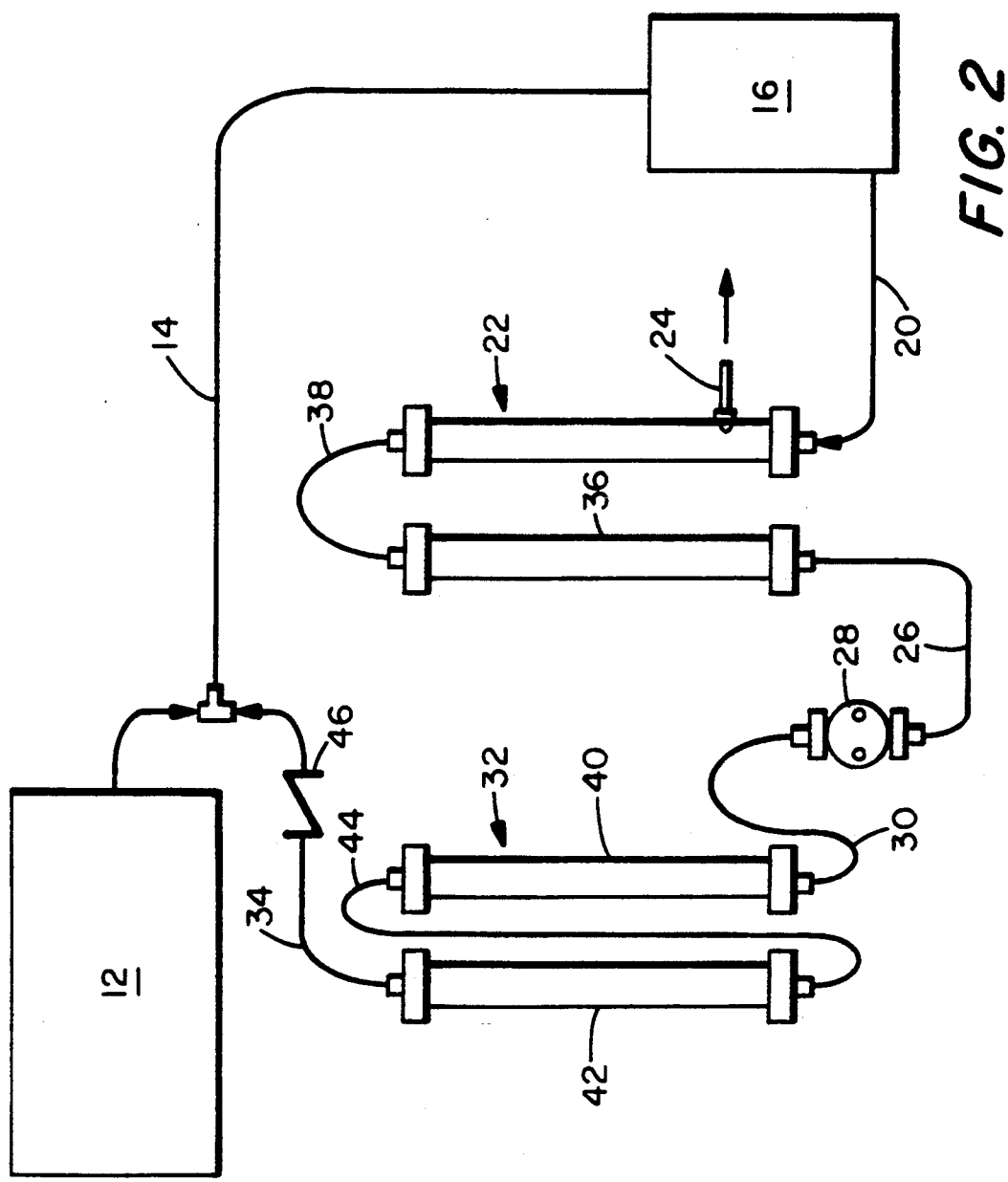
FIG. 2 is a detailed, enlarged illustration of the recycling components of the assembly of this invention.

Referring to FIG. 2, preferred embodiments of this invention comprise a filter unit 22 having a hollow-fiber filter medium of a porosity sized about 0.1 micron. Filter unit 22 is in fluid communication through conduit 38 with a reservoir 36 which in turn feeds into pump unit 28. A preferred embodiment also includes the ion exchange regenerating unit 32 comprising in series a cation regenerating component 40 and an anion regenerating component 42 connected in sequential fluid communication via conduit 44.

A check valve 46 prevents any backflow of eluent into the recycling circuit in the event pump 28 fails.

Figure 3:
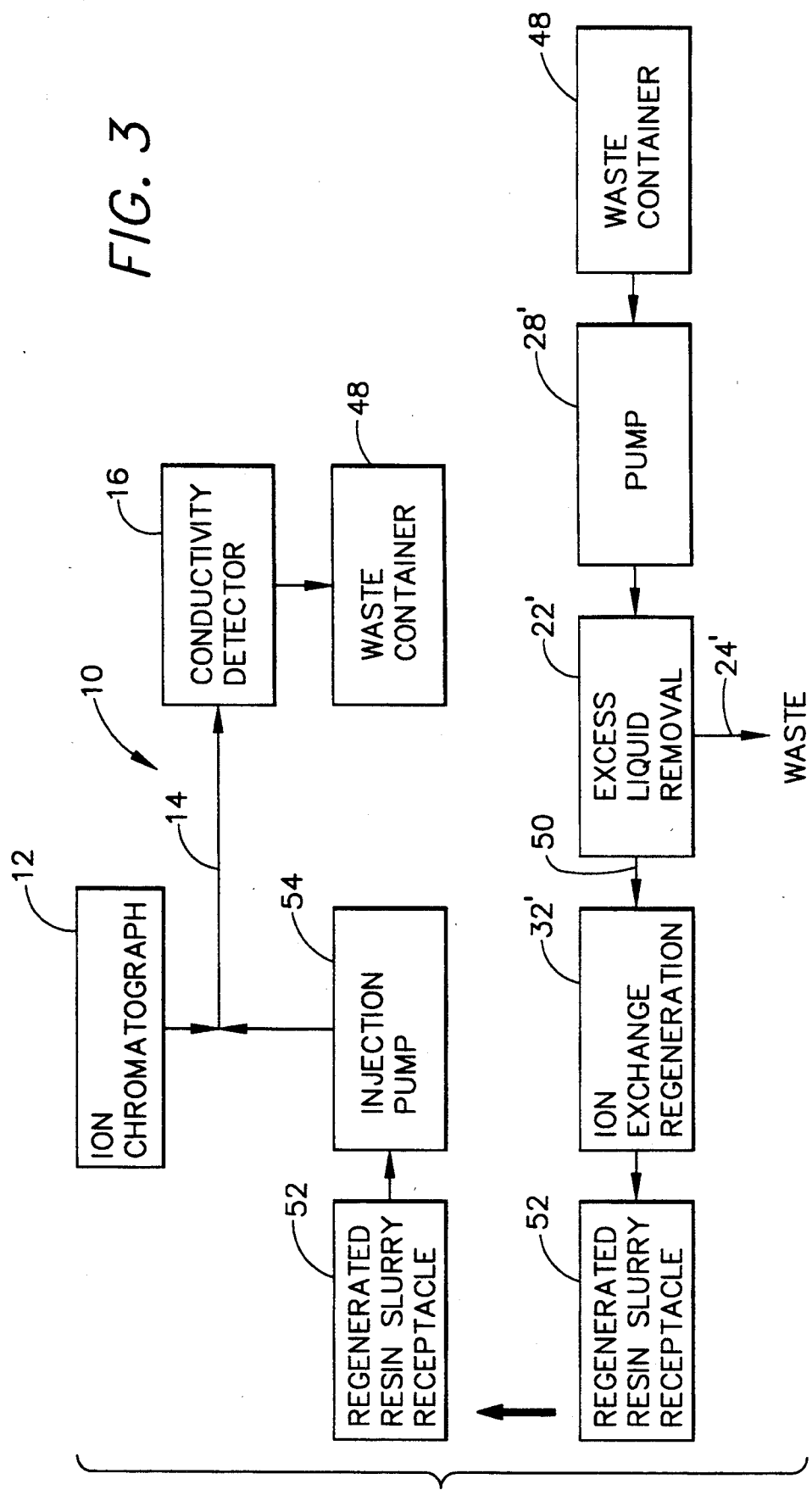
FIG. 3 is a block diagram illustrating an additional embodiment of the subject invention.

In accordance with another embodiment of this invention, the rejuvenating means can be operated separately from the analytical testing means, as illustrated in FIG. 3. In this embodiment of the invention, the spent eluent effluent from the conductivity detector 16 is discharged into a waste receptacle 48 for retention and subsequent rejuvenation pursuant to the measures of this invention. At a convenient or appropriate time, the spent eluent effluent from the conductivity detector 16, which has been collected and retained in waste receptacle 48, is passed through a rejuvenating system or circuit 50 having a fluid impelling pump 28' for driving the spent eluent effluent from the receptacle 48 through a system including in sequence, a filter unit 22' for removing excess liquid from the ion exchange material and an ion exchange regeneration unit 32', and then into a regenerated resin slurry retaining receptacle 52. As in the foregoing embodiment, the filter unit 22' concentrates the ion exchange resin content of the effluent received from the conductivity detector 16 by removing excess liquid phase therefrom as filtrate which is discharged as waste through disposal duct 24', and the ion exchange regeneration unit 32' regenerates the ion exchange material introduced into the eluent dispensed from the ion chromatograph 12 and carried therein as a colloidal resin slurry. Thereafter the regenerated resin slurry collected and retained in receptacle 52 can be reintroduced back into the analytical testing system by injection into conduit 14 with a pump 54.

The recycle system and means of this invention reduces eluent conductivity and enhances analyte conductivity through an ion exchange reaction.

What is claimed is:

1. A system for continuous monitoring of the ionic contents of water samples taken from a nuclear reactor cooling system, comprising an ion chromatograph for receiving said water samples and outputting eluent having an ion content, means for adding a first slurry of ion exchange resin particles having an ion exchange action in a regenerated state to said eluent to form a second slurry, a conductivity detector for analyzing the ion content of said second slurry and then outputting said second slurry with said ion exchange resin particles having an ion exchange action in a spent state, and a solid phase reagent recycling system for regenerating the ion exchange action of said ion exchange resin particles, wherein said solid phase reagent recycling system comprises:

filter means for removing excess liquid from said second slurry output from said conductivity detector to form said first slurry of said ion exchange resin particles having an ion exchange action in said spent state;

means for regenerating said ion exchange resin particles in said first slurry by changing the ion exchange action thereof from said spent state to said regenerated state by ion exchange; and means for pumping said second slurry output from said conductivity detector into said filter means and then into said regenerating means.

2. The system as defined in claim 1, wherein said filter means comprises a hollow-fiber filter.

3. The system as defined in claim 1, wherein said regenerating means comprises cationic ion exchange means and anionic ion exchange means connected in series.

4. The system as defined in claim 1, wherein said regenerating means comprises an ion exchange column, said ion exchange resin particles having a fineness which allows them to pass through said ion exchange column during regeneration without being trapped or adsorbed.

* * * * *